US008398418B2

(12) United States Patent
Nobile et al.

(10) Patent No.: US 8,398,418 B2
(45) Date of Patent: Mar. 19, 2013

(54) ELECTRONIC CONNECTOR HAVING A CLAMPING MEMBER URGING A FLOW CELL TOWARD AN ELECTRICAL CIRCUITRY WITH AN ELECTRICALLY CONDUCTIVE MEMBRANE DISPOSED IN BETWEEN

(75) Inventors: John Nobile, Fairfield, CT (US); George Roth, Fairfield, CT (US); David Marran, Durham, CT (US); William Mileski, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/986,963

(22) Filed: Jan. 7, 2011

(65) Prior Publication Data

US 2011/0217860 A1 Sep. 8, 2011

Related U.S. Application Data

(60) Provisional application No. 61/293,048, filed on Jan. 7, 2010, provisional application No. 61/374,602, filed on Aug. 17, 2010.

(51) Int. Cl.
*H01R 13/52* (2006.01)
(52) U.S. Cl. ....................................................... 439/271
(58) Field of Classification Search .......... 439/271–274, 439/519, 587, 591–593
See application file for complete search history.

(56) References Cited

U.S. PATENT DOCUMENTS

| 5,571,395 | A | 11/1996 | Park et al. |
| 6,802,720 | B2 | 10/2004 | Weiss et al. |
| 6,854,985 | B1 * | 2/2005 | Weiss .............................. 439/91 |
| 6,896,778 | B2 * | 5/2005 | Lauks .......................... 204/400 |
| 7,037,128 | B2 * | 5/2006 | Yaworski et al. ............. 439/276 |
| 7,059,874 | B2 | 6/2006 | Weiss |
| 7,077,659 | B2 | 7/2006 | Weiss et al. |
| 7,223,105 | B2 | 5/2007 | Weiss et al. |
| 7,249,954 | B2 | 7/2007 | Weiss |
| 7,520,761 | B2 | 4/2009 | Weiss |
| 2003/0181071 | A1 | 9/2003 | Weiss et al. |
| 2003/0224633 | A1 | 12/2003 | Weiss |
| 2004/0127071 | A1 | 7/2004 | Weiss et al. |
| 2005/0101167 | A1 | 5/2005 | Weiss et al. |
| 2007/0015375 | A1 | 1/2007 | Weiss |
| 2008/0139020 | A1 | 6/2008 | Weiss |
| 2009/0215296 | A1 * | 8/2009 | Chambers ..................... 439/271 |
| 2010/0248284 | A1 | 9/2010 | Chen et al. |
| 2012/0143531 | A1 | 6/2012 | Davey et al. |

FOREIGN PATENT DOCUMENTS

AU 2003247705 2/2005

(Continued)

OTHER PUBLICATIONS

PCT/US2011/020590 International Search Report Mailed Sep. 15, 2011.

(Continued)

*Primary Examiner* — Chandrika Prasad
(74) *Attorney, Agent, or Firm* — Life Technologies Corporation

(57) ABSTRACT

A leak resistant electrical connector configured as a fluidic barrier between a fluidics device, which may comprise a chemFET sensor, and other electrical circuitry wherein the fluidics device further comprises one or more electrical contacts conductively coupled to one or more electrical contacts associated with the electrical circuitry through the connector.

19 Claims, 7 Drawing Sheets

FOREIGN PATENT DOCUMENTS

| | | |
|---|---|---|
| JP | 08-313479 | 11/1996 |
| JP | 2948049 | 9/1999 |
| JP | 2003254951 | 9/2003 |
| JP | 2009524045 | 6/2009 |
| KR | 19970010981 | 7/1997 |
| TW | 200827886 | 7/2008 |
| WO | 2005013427 | 2/2005 |
| WO | 2008011245 | 1/2008 |

OTHER PUBLICATIONS

PCT/US2011/020590 Written Opinion Mailed Sep. 15, 2011.
PCT/US2007/071984 International Search Report mailed Jan. 24, 2008.
PCT/US2011/020590 International Preliminary Report on Patentability Jul. 10, 2012.

* cited by examiner

ELECTRONIC CONNECTOR HAVING A CLAMPING MEMBER URGING A FLOW CELL TOWARD AN ELECTRICAL CIRCUITRY WITH AN ELECTRICALLY CONDUCTIVE MEMBRANE DISPOSED IN BETWEEN

This application claims priority under U.S. provisional application Ser. No. 61/293,048 filed Jan. 7, 2010 entitled "Fluidics Interface Systems" and U.S. provisional application Ser. No. 61/374,602 filed Aug. 17, 2010 entitled "Fluidics Interface Systems". Both of the foregoing applications are incorporated by reference in their entireties.

BACKGROUND

Rapid and accurate measurement of biological and chemical analytes is important in many fields, including diagnostics, industrial process control, environmental monitoring, and scientific research. A wide range of chemical and biomolecule sensors have been developed that utilize an interface between electrochemical signal-generating processes and electronics for collecting, processing and storing such signals (See for example: Ferrigno et al, Conf Proc. IEEE Eng. Med. Biol. Soc., 1: 4144-4146 (2009); Henry et al, Electrophoresis, 30: 3398-405 (2009); Lingerfelt et al, Meth. Mol. Biol., 385: 103-120 (2007); Ackley et al, U.S. Pat. No. 6,423,271; Ackley et al, U.S. Pat. No. 7,241,419). Chemically sensitive, and in particular, ion-sensitive field effect transistors ("chemFETs" and "ISFETs" respectively) may be used for such measurements (See for example: Bergveld, Sensors and Actuators, 88: 1-20 (2003); Yuqing et al, Biotechnology Advances, 21: 527-534 (2003)). Arrays of such sensors may be fabricated using integrated circuit technologies to obtain spatially distributed and multi-analyte measurements using a single device (See for example: Yeow et al, Sensors and Actuators B 44: 434-440 (1997); Martinoia et al, Biosensors & Bioelectronics, 16: 1043-1050 (2001); Milgrew et al, Sensors and Actuators B 103: 37-42 (2004); Milgrew et al, Sensors and Actuators B, 111-112: 347-353 (2005); Hizawa et al, Sensors and Actuators B, 117: 509-515 (2006); Heer et al, Biosensors and Bioelectronics, 22: 2546-2553 (2007)). Such devices may find applications in research, medicine, industrial process monitoring, and environmental science. Additionally, such devices may be configured to operate with various disposable or consumable components. However, such devices present a design challenge because although they should be easy and convenient to use, they should also be able to provide robust or leak free operation where a liquid sample may be analyzed by the sensor providing output data or electrical signal responses without potential damage to ancillary electronic components or devices.

Therefore, it would be advantageous to provide a device for establishing robust and substantially leak free electrical interface connections that may be used in connection with chemFET sensors or arrays and ancillary or supporting electronic components. It would be further desirable to provide an electrical connection suitable for adaption for use in a chemFET sensor chip or array that is corrosion resistant and able to operate in the presence of a liquid sample.

SUMMARY

In various embodiments, the present teachings are directed towards devices for providing substantially leak-proof electrical connections between chemical sensors. Such sensors may comprise removable or limited use cartridges which contain or are associated with such sensors and other ancillary electronics, such as signal processing circuitry, user interface circuitry, and the like. The sensors may further be configured to operate in the presence of or in proximity to a liquid sample, for example an aqueous sample containing an analyte of interest. The present teachings are further exemplified in a number of exemplary implementations and applications, some of which are summarized below and throughout the specification.

In one aspect, the present teachings are directed to a substantially leak proof electrical connector which provides connectivity between processing circuitry and a sensor cartridge containing an aqueous sample. In certain embodiments, the connector may comprise (a) a socket having an opening and a base, the base being spanned by a sealing membrane which acts as a fluid or liquid barrier. The sealing membrane may further comprise an elastomeric and/or pressure-actuated conductive membrane capable of forming a substantially fluid-proof seal. In various embodiments the socket may be adapted to position, secure, or retain a sensor cartridge in a predetermined or selected orientation. Orientation of the sensor cartridge may further facilitate positioning or alignment of a pattern or series of electrical contacts associated with the sensor cartridge with a corresponding pattern of contacts associated with the processing circuitry or other device designed to be in electrical contact with the sensor cartridge. In various embodiments, the contacts of the processing circuitry may be positioned on opposing sides of the membrane in relation to the sensor cartridge. Furthermore, a clamp assembly or other securing device may be provided such as a relatively close fitting clamp disposed over the socket that positions and secures a sensor cartridge in the socket. The clamp assembly may be adapted to provide a securing pressure or urging of the sensor cartridge with respect to the socket. In various embodiments, the clamp assembly may be used urge or position the electrical contacts of the sensor cartridge into or in close proximity to the membrane to create conductive pathways through the conductive membrane and the corresponding contacts of the processing circuitry.

In another aspect, a connector is provided for use with a sensor cartridge that includes a flow cell for delivering reagents to one or more sensor elements of the sensor cartridge. The flow cell may be configured with one or more inlets and one or more outlets wherein a clamp is further provided which includes a member with one or more fluidic connectors that may be aligned with a portion of the sensor cartridge or the flow cell to form a substantially fluid-tight seal between the fluidic connectors and the portion of the sensor cartridge or the flow cell. In various embodiments, the clamp may provide a substantially fluid-tight seal between the inlets and/or outlets of the flow cell whenever said clamp is in a clamping or securing position.

In still other embodiments, the present teachings provide a substantially leak proof electrical connection between cartridges comprising electronic sensors, such as chemFETs, and devices, components, or appliances containing other processing electronics. In various aspects, the substantially leak proof electrical connection protects the devices, components and appliances from potential fluid spills, fluidic intrusion, and/or liquid contact. Furthermore, the connection further provides corrosion resistance and/or reduces the potential for electrical shorting or other such hazards. The present teachings also provide a number of techniques for establishing an electrical connection between a first pattern of electrical contacts (for example those associated with a sensor cartridge) and a second corresponding pattern of contacts (for example those associated with a processing circuit or component).

In certain embodiments, an elastomeric, conformable, or pressure-actuated conductive membrane is provided and may compensate for various anomalies, imperfections, or surface features arising from the construction of either the sensor cartridge or the pattern of electrical contacts associated with the processing circuitry. Still other embodiments utilize at least partially flexible circuits to accommodate or compensate for anomalies, imperfections, or surface features arising from the construction of sensor pads, sensor cartridges, or electrical contacts associated with the processing circuitry. In various aspects, the electrical contacts of the processing circuitry may undergo a re-plating operation to provide more prominent or robust electrical contacts in relation to the remaining circuitry. Other embodiments of the present teachings describe use of interspersed areas of conductive and non-conductive silicon which may be used in a complementary or analogous manner as the elastomeric, conformable, or pressure-actuated conductive membrane. In still another aspect of the present teachings, at least a portion of the electrical connectors in the membrane, sensor cartridge or processing circuitry may be fabricated from substantially the same material or of a material that prevents or is resistant to corrosion including galvanic corrosion. Connectors in accordance with the present teachings may be adapted for sensor arrays that are connected to or associated with a fluidic reagent delivery system. One exemplary system that may be configured to benefit from the present teachings is described by Rothberg et al, U.S. patent publication 2009/0127589 which is incorporated herein by reference.

In other embodiments, the present teachings describe a fluid-tolerant electrical connector comprising: a conformable electrically conductive membrane configured as a fluidic barrier between a fluidics device and other electrical circuitry wherein the fluidics device comprises one or more electrical contacts conductively coupled to one or more electrical contacts associated with the electrical circuitry through the membrane; wherein the one or more electrical contacts of the fluidics device are selectively conductively coupled to one or more corresponding contacts associated with the electrical circuitry through conductive pathways formed in the membrane while fluid contained in the fluidics device is substantially prevented from contacting the electrical circuitry by the membrane.

In further embodiments, the present teachings describe a method for establishing an electrical connection between a fluidics device and other electrical processing circuitry, which include: positioning a conformable electrically conductive membrane in proximity to the fluidics device and the other electrical processing circuitry forming a substantially fluid-proof barrier; providing electrical conductivity between electrical contacts associated with the fluidics device and electrical contacts associated with the other electrical processing circuitry through the membrane via one or more conductive pathways present in the membrane by urging the fluidics device and the electrical processing circuitry in proximity to one another with the membrane disposed therebetween wherein connectivity is established between the electrical contacts of the fluidics device and electrical contacts associated with the other processing circuitry through the conductive pathways present in the membrane; and transmitting electrical signals from the fluidics device through the membrane to the other electrical processing circuitry while the membrane prevents fluid from contacting the other electrical processing circuitry.

In still further embodiments, the present teachings describe an electrical connector for a fluidics device comprising: a conductive membrane forming a fluidic barrier between the fluidics device and other electrical circuitry wherein the fluidics device comprises one or more contacts to be conductively coupled to one or more contacts associated with the electrical circuitry wherein the one or more contacts associated with the electrical circuitry and the one or more contacts associated with the fluidics device are positioned on opposing sides of the membrane; and conductive pathways formed through the membrane configured to selectively conductively couple the one or more contacts associated with the fluidics device with one or more corresponding contacts associated with the electrical circuitry thereby providing one or more signal transmission pathways for transmitting signals in response to analytes contained in the fluidic device while the membrane remains substantially impermeable to fluid to protect the electrical circuitry.

BRIEF DESCRIPTION OF THE DRAWINGS

The skilled artisan will understand that the drawings, described herein, are for illustration purposes only. The drawings are not intended to limit the scope of the present teachings in any way.

DETAILED DESCRIPTION OF SELECTED EMBODIMENTS

Figure 1A:
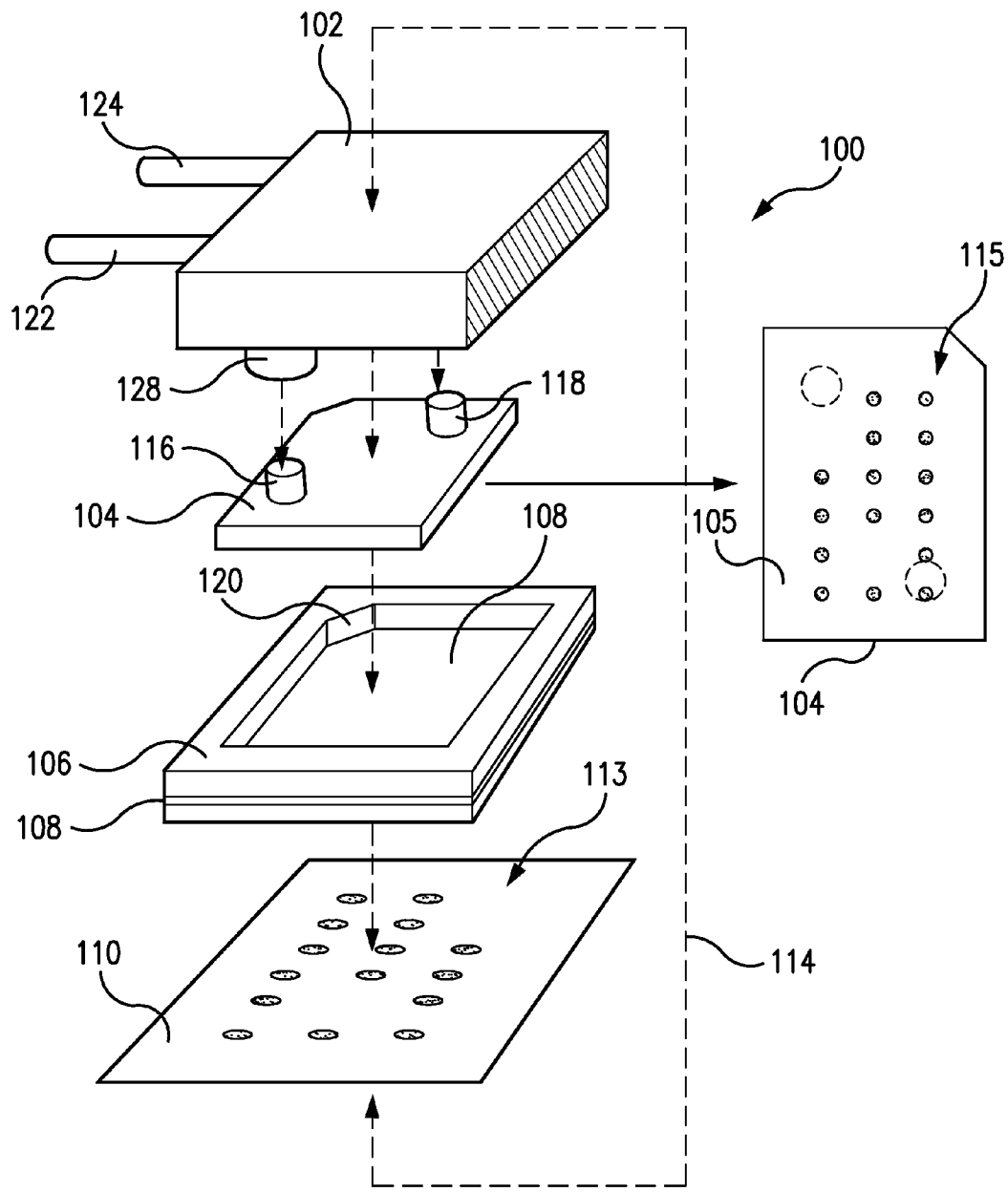
FIG. 1A illustrates one embodiment of the fluidic interface system of the present teachings wherein a portion of a clamp assembly comprises a fluidics connection to a sensor cartridge.

The present teachings may employ, unless otherwise indicated, conventional techniques and descriptions of mechanical engineering, electronics, fluid mechanics, and materials science, which are within the skill of the art. Such conventional techniques include, but are not limited to, design and fabrication of fluidics and microfluidics devices, and the like. Specific illustrations of suitable techniques can be had by reference to the example herein below. However, other equivalent conventional procedures can, of course, also be used.

It will be understood that the following description of some embodiments is merely exemplary in nature and is in no way intended to limit the present teachings, applications, or uses. Although the present teachings will be discussed in some embodiments as relating to fluidic analysis and processing, such as nucleic acid sequencing using chemically sensitive or ion sensitive FETs sensors, such discussion should not be regarded as limiting the present teachings to only such applications.

The section headings and sub-headings used herein are for general organizational purposes only and are not to be construed as limiting the subject matter described in any way.

In various embodiments, the present teachings describe a fluidic interface system which may be adapted for use with sample analysis devices that involve analyzing a liquid sample containing analytes of interest using one or more electronic sensors. In certain aspects, the electronic sensors comprise one or more electrical contacts which couple the sensor to other electronic components. A portion of the electronic sensor may be exposed to the liquid sample and it is desirable to insure that the liquid sample remain sequestered away from the other electronic components while at the same time providing electrical connectivity between the sensor and the other components. In an exemplary application using a chemFET array comprising a plurality of chemically sensitive or responsive sensors, the fluidic interface system should provide a mechanism to provide connectivity between the contacts on the chemFET array or sensor chip to contacts associated with a corresponding interconnect surface. The interconnect surface further provides electrical connectivity to ancillary electronic components while at the same time isolating them from potential sample liquid exposure or intrusion.

In other aspects of the present teachings, the fluidic interface system provides mechanisms to address and/or overcome warping, surface anomalies or other manufacturing imperfections of either the sensor array or the corresponding interconnect surface. In certain instances, imperfections or the like may result in the sensor array or corresponding interconnect surface to not position evenly or provide a non-uniform contact between the sensor array and the interconnect surface resulting in partial or improper connectivity between the two components.

A further feature of the fluidic interface system of the present teachings is that the device may be configured to be resistant to corrosion resulting from exposure to the liquid sample including potential galvanic corrosion that may occur for example between a chemFET sensor array and the electronic processing device adapted to receive or interact with the array. Susceptibility to corrosion may also be mitigated for the electrical contacts on the corresponding interconnect surface, which may result for example where one metal at the interface of electrical contact is fabricated from a different type of metal than that of the electrical contacts of the chemFET sensor or the electrical contacts of the corresponding surface.

As will be described in greater detail hereinbelow, applications of the present teachings are useful for providing a component capable of establishing a fluidic barrier and/or leak-proof electrical interface between chemFET sensors chips and ancillary electronic components. In various embodiments, the interface may be used to establish an electrical connection between contacts on a chemFET sensor chip and contacts on the corresponding surface (which electrically connects to ancillary electronic components). Such a component may further be configured to reduce or eliminate galvanic corrosion that might otherwise occur between the device and either the chemFET sensor chip or the electrical contacts on the corresponding surface.

One embodiment of the present teachings is illustrated in FIG. 1A. Elements of connector (100) include clamp member (102), socket (106) containing anisotropic conducting membrane (108), surface (110) containing electrical contacts (113) to processing electronics, and forcing element (114) for providing a clamping action. Forcing or coupling element (114) urges clamp member (102) against sensor cartridge (104) which, in turn, is urged against anisotropic conducting membrane (108) which, in turn, provides one or more electrically conductive pathways between contacts (115) on the bottom (105) of sensor cartridge (104) and corresponding contacts (113) of the processing electronics on surface (110). Forcing or coupling element (114) can be solely or partially mechanical (as exemplified below), electrically actuated via solenoids, motors, hydraulics, or operated in other ways manually and automatically as will be appreciated by one of skill in the art. In various embodiments, it is preferable for the forcing or coupling element (114) to urge by application of force or pressure evenly over sensor cartridge (104) so that the one or more conductive pathways between electrical contacts through membrane (108) are substantially uniformly engaged. Additionally, a uniform urging force may be desirable so that membrane (108) does not evidence localized wear or compression over time or through repeated use.

Figure 1B:
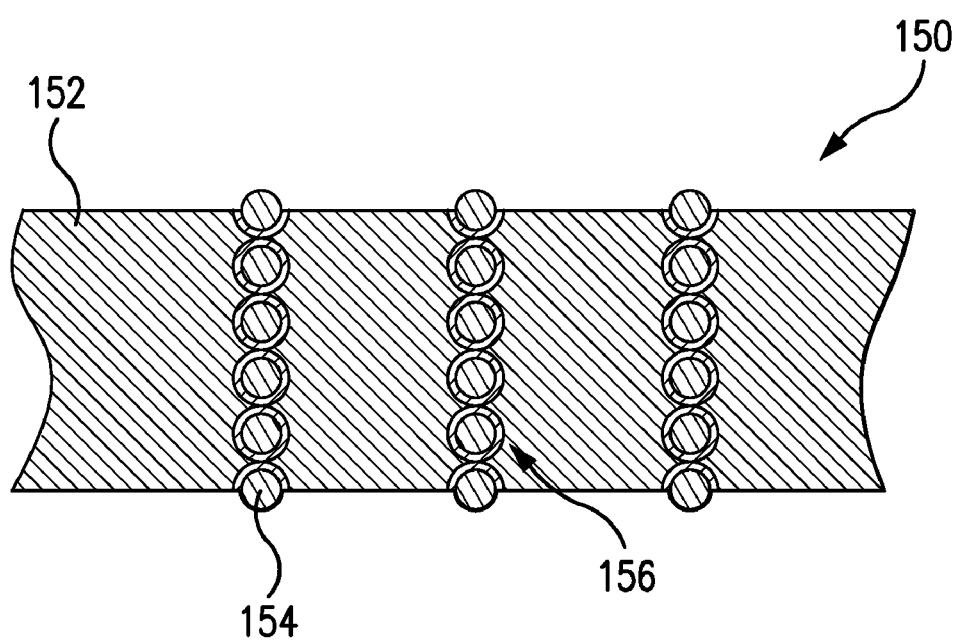
FIG. 1B is a cross sectional view of an exemplary anisotropic conducting elastomer.

An example of an anisotropic conducting membrane or elastomer (108) is illustrated in FIG. 1B. In various embodiments, commercially available materials may be used to fabricate such conformable or elastomeric membranes (e.g. Paricon Technologies Corp. (Fall River, Mass.), which manufactures the PariPoser interconnection system and the like). In various embodiments, such membranes (150) may comprise an elastomeric material (152) in which columns (156) of conductive particles (154) are aligned substantially perpendicularly to the plane of the membrane. In such configurations, where electrical contacts touch opposing sides of the membrane, a conductive pathway is established between them. These electrical contacts may further be isolated from other contacts touching the membrane at other locations and may further provide connectivity for multiple independent electrical contacts based upon the configuration and orientation of the membrane. In accordance with various embodiments of the present teachings, the membrane may be fabricated from a material that is substantially impermeable and/or non-reactive to fluids and chemical components contained therein, particularly aqueous fluids and reagents associated with the sample analysis.

It will be appreciated that the materials used to form the membrane may be selected from a number of different materials as will be described in greater detail hereinbelow. Additionally, the dimensionality and thickness of the membrane can be tailored for specific applications or instrumentation. Likewise the inter-membrane connectivity may be provide by conductive materials other than beads and may be present in orientations other than that exemplified in FIG. 1B. For example, electrical connectivity through the membrane may result from flexible wires or traces which are aligned with the electrical contacts on the receiving or contacting surfaces of the membrane. In such instances, the membrane's conformability characteristics may allow deformation of portions of the membrane when engaged with the sensor cartridge and/or the processing electronics. The electrical conductivity is further preserved as the inter-membrane conductivity features are also tolerant to deformation of the membrane and thus may preserve conductive pathways between the surfaces of the membrane.

As previously described, the membrane may be advantageously used to provide electrical connectivity between desired components such as the sensor chip and processing electronics even where the electrical contacts or surface features of the components are not perfectly matched. For example, imperfections in the construction of the sensor cartridge (105) or the surface (110) can result in some of the contacts (115) of the sensor cartridge (104) and the corresponding contacts (113) of the processing electronics on surface (110) to not maintain good electrical conductivity or connectivity when positioned in proximity to one another due to partial contact or misalignment of at least a portion of the contacts. Additionally, the required urging force provided by the coupling element (114) may be reduced by use of the membrane which may aid in providing more uniform connectivity between the contacts rather than necessitating a relatively large urging force to conductively join each of the desired contacts. The reduction in urging force required further reduces the risk of damaging or breaking components within the system which might otherwise occur to establish the electrically connective pathways between components. Such damage might occur as a result of the force applied to insure connectivity between desired contacts or through repeated use or operation with multiple sensors. In certain instances, the membrane may also be used in situations where warping or deformation of the sensor cartridge or the corresponding contacts of the processing electronics may occur which cause either the sensor cartridge or surface (110) contacts to lie outside of a substantially 2-dimensional plane. As a result, without the membrane, some contacts between the sensor cartridge (115) and the surface (113) may not readily electrically connect when positioned substantially adjacent to one another in a desired orientation.

In one embodiment of the present teachings, the elastomeric material (152) of the membrane (150) is designed such that the elastomeric material (152) in combination with the forcing element (114) compensates for any imperfections in the construction of the individual components, such that electrical connections are established between desired contacts (115) on the sensor cartridge (104) and the corresponding contacts (113) of the processing electronics on surface (110). In another embodiment, either the surface (110) which contains the contacts (113) of the processing electronics, or the sensor cartridge (104) which contains the contacts (115) may be manufactured using flex circuit technology. In various embodiments, flex circuitry relates to technology for assembling electronic circuits by mounting electronic devices or components on at least partially flexible substrates (such as a flexible polymer, plastic, or nylon surface).

In another embodiment of the present teachings, either the contacts (115) on the sensor cartridge (104) or the contacts (113) of the processing electronics on surface (110) are selectively re-plated during manufacturing. With regard to the surface (110), the contacts (113) a portion or substantially all of the contacts may undergo a re-plating operation in order to alter the physical geometry of desired contacts so as to improve connectivity between components. In various embodiments, the re-plating operation may include creating thicker or taller contacts (113), capping the contacts, thinning or resizing the contacts, or performing other modifications to at least a portion of the contacts in order to obtain a desired height and/or profile for the electrical connections. The aforementioned re-plating operations may further be utilized in connection with the anisotropic conducting membrane (108) to establish positive or uniform connectivity of the contacts (115) on the bottom of sensor cartridge (104) with the contacts (113) of the processing electronics on surface (110). In various embodiments, the re-plating operations cause other areas besides the contacts (113) on the surface (110) to retain substantially their original height, profile, and/or thickness.

In an exemplary circuit board embodiment, selective re-plating may be accomplished by masking at least a portion of the circuit board that is not desirably re-plated and subsequently passing the circuit board through the plating process thereby preserving the surface features or contour of contacts or surfaces that have been masked. In another embodiment of the present teachings, the conducting membrane (108) may be comprised of interspersed areas of conductive and non-conductive material such as a polymer, plastic, nylon, silicone, glass or other material. The conducting membrane may further comprise one or more column of conductive material such as metal impregnated or conductively modified polymer, nylon, silicone, or other suitable material or mixtures thereof in selected areas to contact, join, or mate the contacts (115) on the bottom of sensor cartridge (104) and the corresponding contacts (113) of the processing electronics on surface (110). In various embodiments, the column may be substantially perpendicularly aligned to the plane of the membrane. The conductive column may create or establish a desired or uniform electrical connection from the top to the bottom of the membrane (108), similar to the columns (156) of conductive particles (154). The conducting membrane (108) may further comprise portions of non-conductive or insulating material (e.g. polymer, nylon, silicone, glass, or other suitable material or mixture thereof) in areas between the different contacts (115) on the bottom of sensor cartridge (104), to reduce or eliminate undesired cross-talk or conductivity between contacts (115) on the bottom of sensor cartridge (104). In accordance with the present teachings, the membrane may be manufactured such that it is impermeable to and/or resilient to fluids, particularly aqueous fluids and reagents/chemicals which might come into contact with the membrane.

In various embodiments, it may be desirable to prevent oxidation or galvanic corrosion of selected components within the system. Such oxidation or galvanic corrosion may occur for example between the electrical contacts (115) on the bottom of sensor cartridge (104) and the anisotropic conducting membrane (108), or the electrical contacts (113) of the processing electronics on surface (110) and the anisotropic conducting membrane (108). In certain embodiments, the anisotropic conducting membrane (108), the contacts (115) on the bottom of sensor cartridge (104), and the contacts (113) of the processing electronics on surface (110) may be fabricated from or coated with substantially the same or similar metal or formed to create conductive surfaces of compositions which are compatible and/or resistant to oxidation or galvanic corrosion. In one such embodiment, the contacts (115) on the bottom of sensor cartridge (104) and corresponding contacts (113) of the processing electronics on surface (110) may be gold-plated with the columns (156) of conductive particles (154) in the anisotropic conducting membrane (108) also being gold-plated. In such instances, gold-plating the columns (156) of conductive particles (154) in the anisotropic conducting membrane (108) may aid in reducing oxidation or galvanic corrosion which might otherwise occur between the membrane (108) and the contacts (115) on the bottom of sensor cartridge (104), or the membrane (108) and the contacts (113) of the processing electronics on surface (110). In additional to coating with gold, it will be appreciated that other coatings or materials may be used to confer the desired resistance to oxidation or corrosion. Thus, other metals or conductors may be used to confer a desired oxidation and/or corrosion resistant property. In certain embodiments, the existing material used to form the conductor may be chemically altered or modified directly rather than coated with a different material.

Returning to FIG. 1A, clamp member (102) may comprise conduits (122 and 124) and passages (not illustrated) for transferring fluid through fluid connectors (exemplary element 128 shown) into and out of sensor cartridge (104) through inlet (116) and outlet (118) when in a clamp-closed configuration. In addition to providing a fluidic connection, when in such configuration or position, sensor cartridge (104) may be forced or urged onto conducting membrane (108) to establish, creates, or maintain conductive pathways between contacts (115) on the bottom of senor cartridge (104) and corresponding processing electronics contacts (113) on surface (110).

Other embodiments of the present teachings are illustrated in FIGS. 2A-2F. Selected embodiments may include features such as: Substantially the same action and/or force associated with the clamp (200) may provide both electrical connectivity & fluid port sealing with respect to the chip (202). The clamp design may also protect underlying electronics components within the system such as a PC board containing processing electronics from fluid spills and/or reagent/liquid contamination. Furthermore, a lever or actuator (208) may be provided with a substantially high mechanical advantage and/or a retention feature to engage the sensor chip (202) in a clamped position and secured position. Furthermore, a compression-spring mechanism may be provided in connection with the clamping mechanism to at least partially reduce the required clamping energy or to facilitate urging of the various components together. To facilitate fluidic engagement with the sensor chip (202) tapered fluid-port bosses and/or receivers may be utilized to facilitate engagement of the fluidic ports and provide a self-aligning feature for the fluid connections. These fluid-ports may further comprise elastomeric seals or gaskets (Exemplified in FIG. 2C) to further enhance or improve the sealing and/or leak resistance of the system.

In various embodiments, a mechanically floating fluid manifold may be provided that at least partially self-aligns for example in X & Y directions. In various embodiments, the manifold may also be configured so as to possess an angular float to allow substantially equivalent forces to be applied to each of the fluidic seals or ports. Certain configurations also provide for fluidic seals that permit or direct a substantially lateral flow path so that various sizes, profiles, or configurations of sensors or flowcells can be accommodated. Additionally, the clamping mechanism may provide accessibility to desired components by its movable or pivoting orientation. For example, the clamping mechanism may be configured so as to open by pivoting sufficiently to provide access to the top of the sensor or flowcell to permit desired operations such as fluidic/reagent introduction or withdrawal. (See exemplary positioning of the clamping mechanism shown in FIGS. 2A-2F) These operations may include manual activities such as pipetting into the flowcell ports which may be made accessible to the user when the clamping mechanism is in the open position. Furthermore, the sensor or flowcell ports may be designed to accept, mate with and/or seal with components having standardized dimensions (such as a 1 mm outer diameter tapered pipette tip).

Figure 2A:
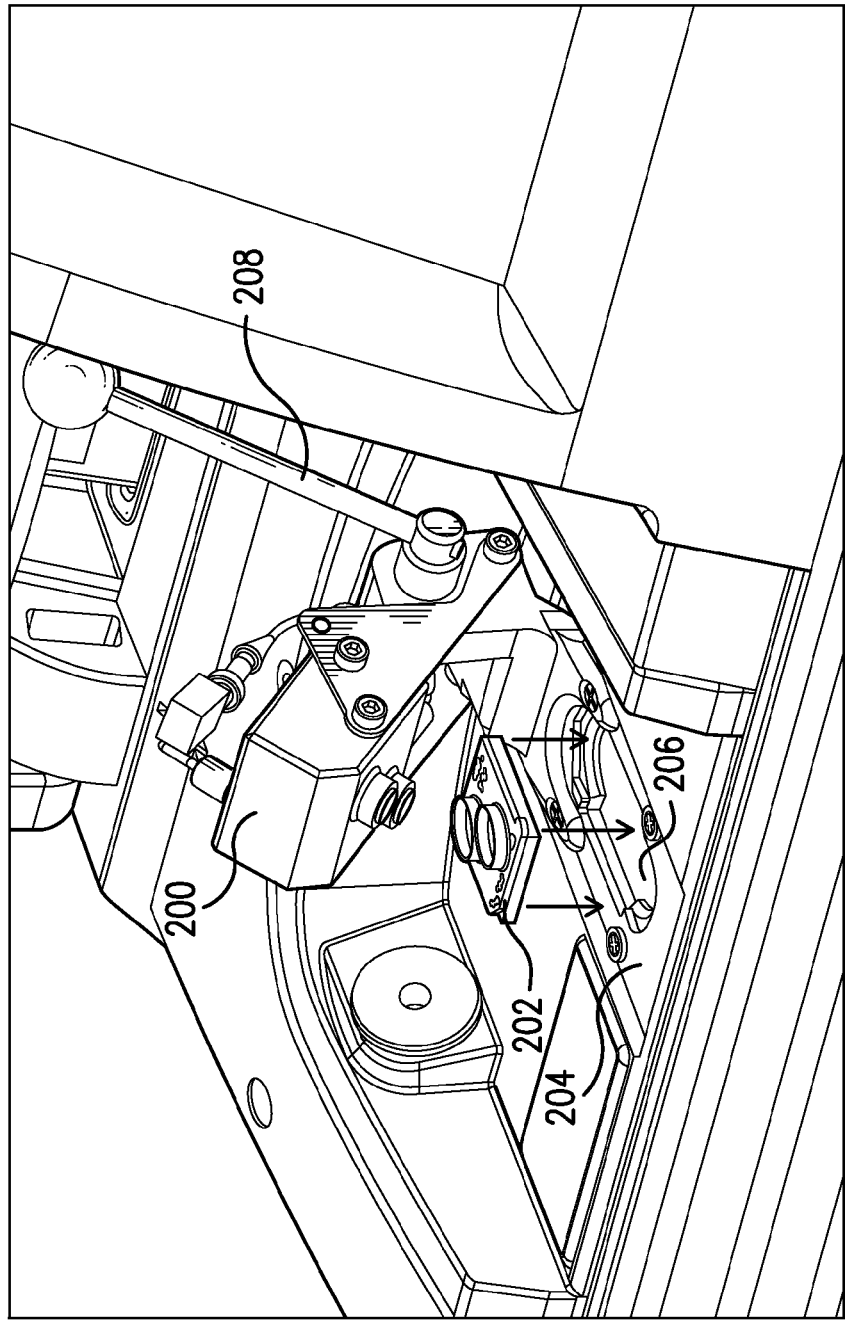
FIG. 2A illustrates an embodiment of the present teachings adapted for use with a nucleic analysis device employing a sensor cartridge comprising a chemFET array. The clamp is shown in an open position with the sensor cartridge suspended (for illustration purposes) between fluidics connectors of a top clamp member and a socket for positioning the sensor cartridge.

As exemplified in FIG. 2A, clamp member (200) may be positioned in a substantially open position allowing positioning of the sensor or flowcell (202) within or removal from the instrument (201). Likewise, as previously discussed when clamp member (200) resides in the substantially open position, as shown in FIG. 2A, additional operations such as manual fluidic operations may be performed on the sensor or flowcell (202). The clamp member (200) may further be operationally associated with a mechanical forcing element comprising a spring-actuated self-locking mechanism operated by actuator or lever (208). One embodiment of such a mechanism is exemplified in FIGS. 2A-2G wherein the actuator or lever (208) operates in connection with a compression spring assembly (222) such that in the closed position the assembly may be "locked" into position to insure positive fluidic and/or electrical connectivity. In other embodiments, the mechanical forcing element may comprise an automatic or electrically operated component such as a servo driven actuator which applies a suitable force to actuate and position the clam member (200) as desired. Clamp member (200) may also include fluidics connectors for delivering reagent to sensor cartridge (202). In FIG. 2A, the sensor cartridge is not mounted but rather is shown suspended under clamp member (200) and above socket (204) depicting an exemplary relative positioning of the components with respect to one another. In the illustrated embodiment, anisotropic conducting membrane (206) is shown at the base of socket (204) and provides desired alignment and connectivity for the sensor cartridge (202) with the instrument as described previously. It will be appreciated that the membrane (206) may be positioned in a number of manners such as being integrated into or attached to a surface of the sensor cartridge (202) and not necessarily limited to those depicted in the illustrations.

Figure 2B:
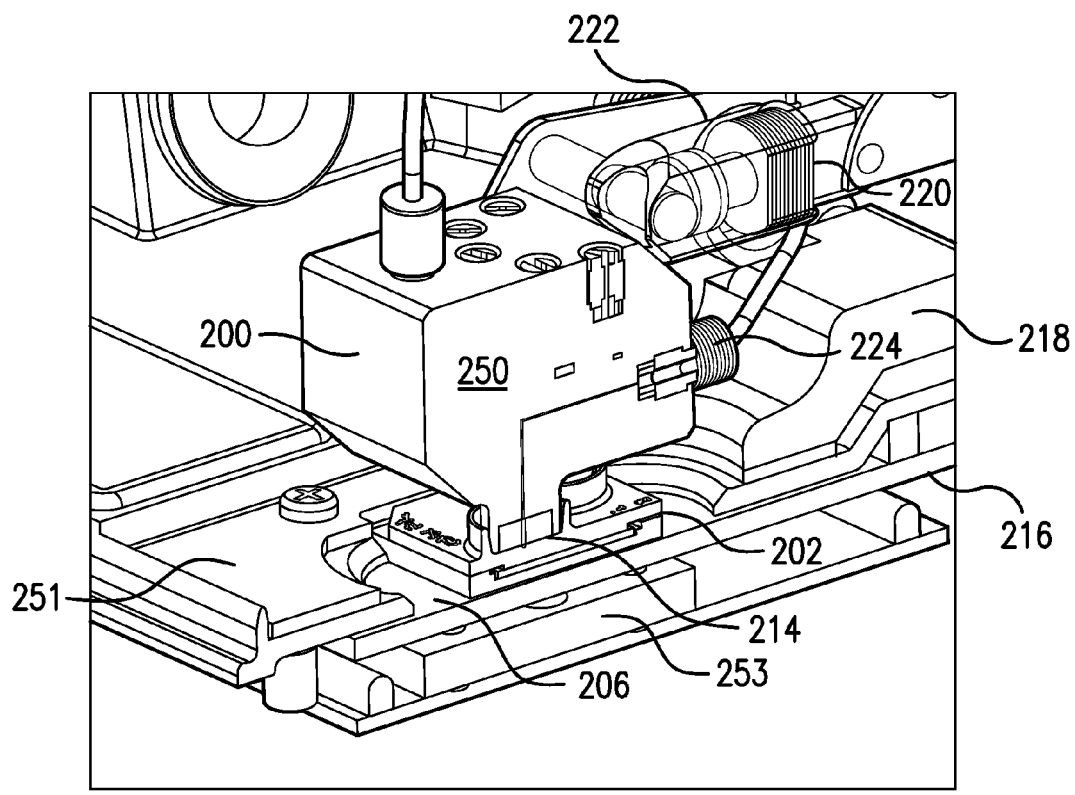
FIG. 2B is a cut-away view of the clamp of FIG. 2A in a closed position.

FIG. 2B illustrates a cut-away view of the device of FIG. 2A with the clamp member shown in a substantially closed position. Clamp member (200) may be configured to retain the sensor cartridge (202) (also referred to as the "flowcell and/or chip assembly") and firmly urge the cartridge (202) against anisotropic conducting membrane (206) (also referred to as "silicone ball-wire interposer"). Clamp member (200) may be operationally associated with spring actuated mechanism (222) (also referred to a "compressible spring assembly") for generating a substantially evenly distributed downward force onto clamp member (200) and through contact sensor cartridge (202). Clamp member (200) further serves as a fluid manifold for delivering reagents to and from sensor cartridge (202) through conduit (224) and other conduits not shown. FIG. 2B also shows that the device comprises a metal stiffener plate (251), a metal back-up plate (253), an elastomeric seal (214), a PC board (216), a clamp body (218), and a compression spring or group of wave washers (220).

Figure 2C:
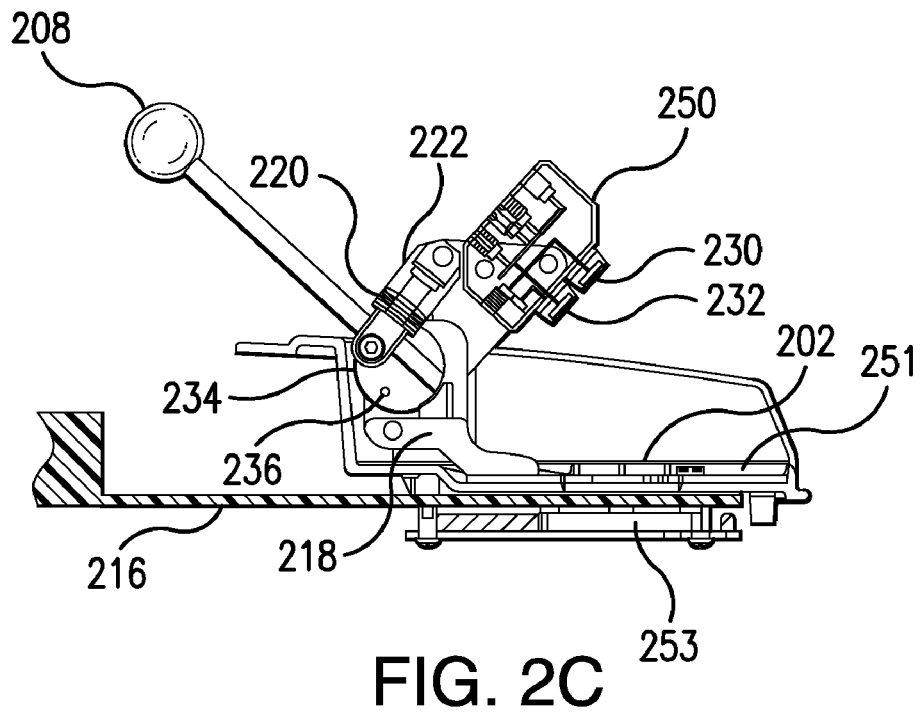
FIGS. 2C-2G show different positions of the clamp of FIG. 2A which illustrate a self-locking feature of one embodiment of the clamp.
Figure 2D:
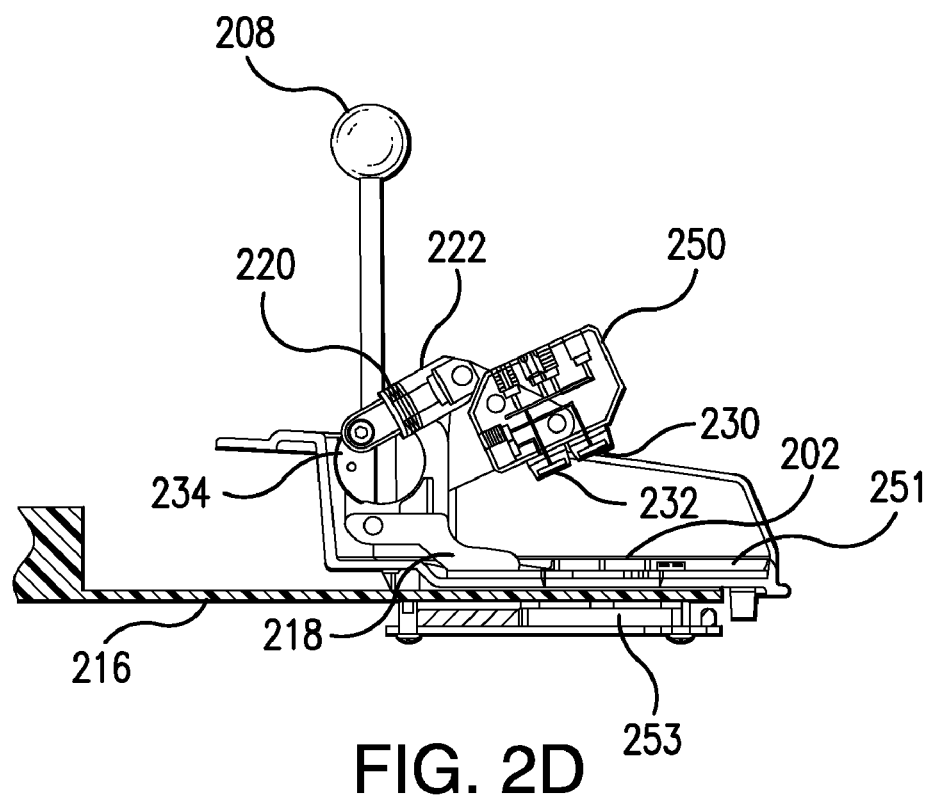
Figure 2E:
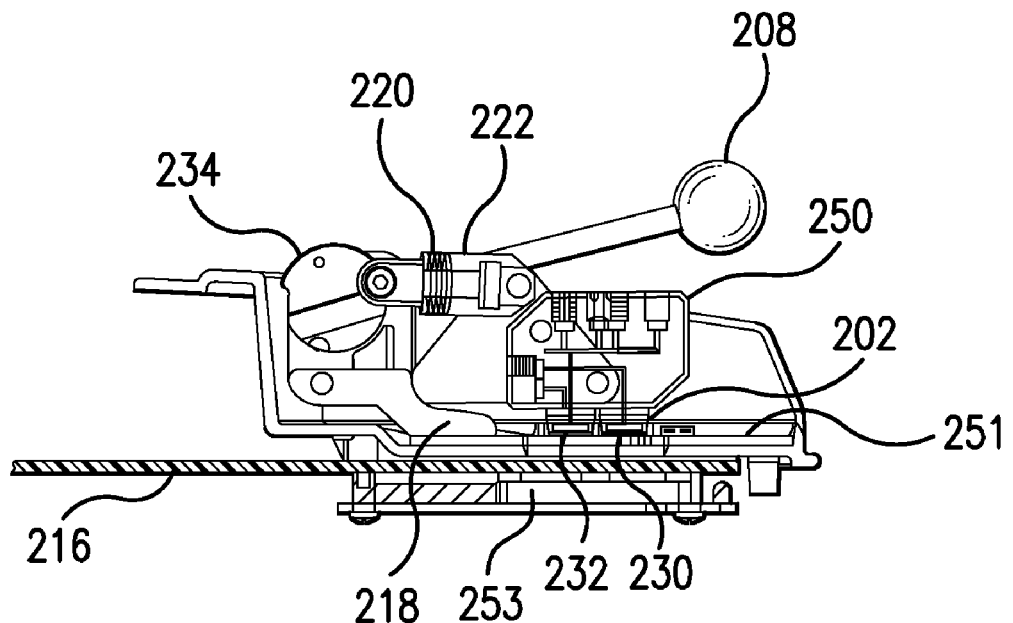
Figure 2F:
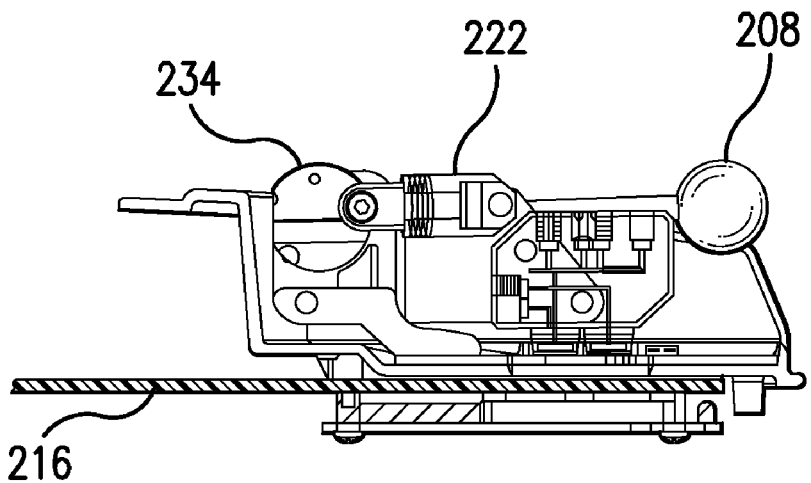
Figure 2G:
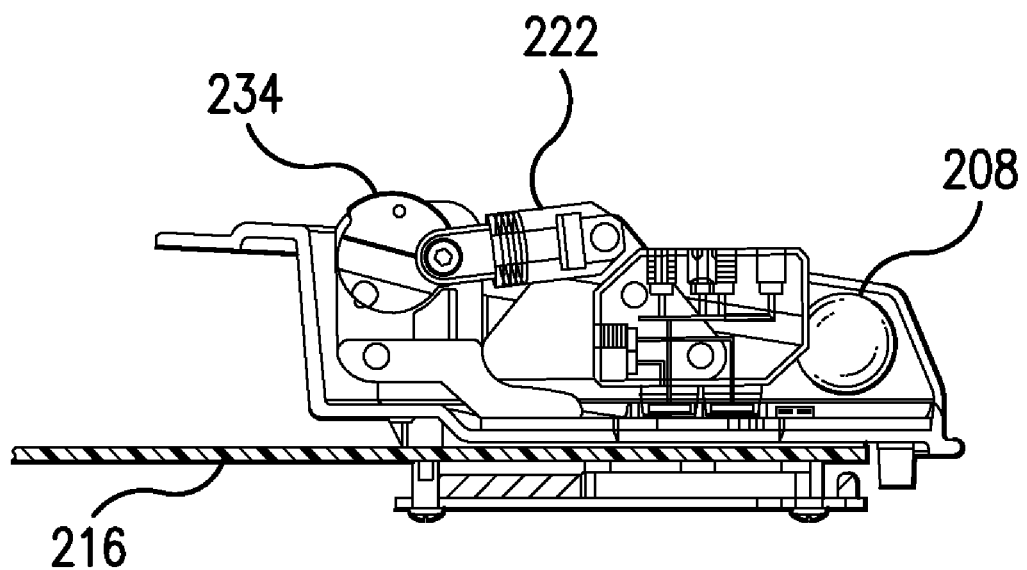

FIGS. 2C-2G show further operational embodiments of the present teachings using an exemplary manual actuator assembly for imparting the urging and positioning force to the instrument assembly which retains the sensor array or flowcell (202). As previously discussed, the configuration of the components for retaining the flowcell (202), the flowcell configuration itself, and the mode of imparting position or securing force to the flowcell (202) may be modified as desired, for example using an automated actuator assembly versus a manual actuator without departing from the scope of the present teachings. Likewise, while a singular flowcell is depicted in the Figures, the system may be designed to accommodate multiple flowcells as desired. As shown in FIG. 2C, the chip clamp (200) may be positioned in a fully open position through the use of the actuator assembly or lever (208) to disengage the fluid manifold (250) and associated fluid transfer ports from the flowcell (202). An assembly operably connected to lever (208) can comprise an eccentric (234) and a ball detent (236). The fluid transfer ports may comprise elastomeric seals (230), (232) positioned in a manner so as to engage with one or more mating or complementary ports on the flowcell (as shown in FIG. 2A) to provide a substantially fluid-tight or leakproof seal when the chip clamp resides in a closed position. Additionally, various structural enhancements may be included within the system such as a stiffener (251) and/or back-up plate (253) to improve the structural integrity of the mechanism. In various embodiments, such features may be used to provide a substantially rigid surface to engage the flowcell (202) aiding in maintaining a desired position or profile of the flowcell (202). In FIG. 2D the chip clamp is shown in a partially open position. In FIG. 2E the chip clamp is shown in a lowered position with manifold (251) in full contact with flowcell (202), before compression spring (220) is fully loaded. In FIG. 2F the chip clamp is shown in a lowered position with compression spring (220) fully loaded. As can be seen in FIG. 2F, actuator or level (208) is almost horizontal whereby eccentric (234) is in a top dead center position. In FIG. 2G the chip clamp is shown in the fully lowered and locked position with compression spring (220) partially loaded or compressed. As can be seen in FIG. 2G, actuator or level (208) is in a position below the horizontal whereby eccentric (234) is beyond a top dead center position and actuator or lever (208) is locked into position.

The step-wise operation and positioning of the various components illustrated in FIGS. 2C-2G depict one possible operational embodiment for securing the flowcell and engaging the fluidic and electronic components. The configuration and components as illustrated provide a "self-locking" feature such that the flowcell (202) may be retained in a selected position with sufficient force to urge the appropriate electrical and fluidic contacts and connections providing a substantially leak-free system with good electrical connectivity. It will be appreciated that other configurations may be also used or adapted based on the preference or requirements of the system. For example, as previously described operation of the spring actuated clamp (222) may be controlled by lever (208) or an automated actuator assembly such as a motor or servo-driven mechanism without departing from the scope of the present teachings.

While the present teaching has been described with reference to several particular example embodiments, those skilled in the art will recognize that many changes may be made thereto without departing from the spirit and scope of the present teaching. The present teachings are applicable to a variety of sensor implementations and other subject matter, in addition to those discussed above. It will be understood that the conformable conductive membrane configurations described above may be adapted for use with components other than flowcells in which an electrically conductive fluid-tolerant connection/or coupling is desirable. Additionally, the number of discrete electrical contacts which are to be coupled may vary widely in number from as little as one to hundreds, thousands, millions, or more connections. Other configurations of membrane connections may also be established including "sandwiching" a desired component between two or more membranes or partially or completely enclosing or encapsulating the desired component within or about the membrane to achieve the desired positioning, coupling, or connectivity effects. Similarly, the membrane may be formed as an integrated member of the desired component and/or fashioned in shapes or structures other than as a substantially flat or planar membrane to achieve a desired positioning, coupling, or connectivity.

As used herein, "microfluidics" devices or components, "fluidics" device or components, "fluid transfer" devices or components may comprise integrated systems having one or more chambers, ports, and/or channels that may be interconnected and/or in fluid communication with various other components within the system. These components may further be designed for containing, transporting or carrying out one or more analytical reactions or process, either alone or in cooperation with an appliance or instrument that provides additional support functions, such as sample introduction, fluid and/or reagent driving or delivery features, temperature control mechanisms, sample and/or analyte detection systems, data collection, data processing and/or data integration systems, and the like. The aforementioned devices may further include valves, pumps, conduits and other fluid transfer or fluid containment components with functional coatings or treatments applied, such as for example specialized coatings on the interior walls to substantially reduce or prevent adsorption of sample components or reactants, to facilitate reagent movement by electro-osmosis, or to impart other desired effects or properties. Such devices may be fabricated in or as a solid or formed substrate, which may be for example glass, plastic, or other polymeric materials, and may have an at least partially planar format or surface for facilitating detecting and/or monitoring sample and reagent movement, especially via optical or electrochemical methods.

Features of the aforementioned devices may have cross-sectional dimensions of less than a few hundred square micrometers and passages may have capillary dimensions, e.g. having cross-sectional dimensions of from about 500 µm to about 0.1 µm although other dimensionalities may be utilized readily as well. Microfluidics devices may have volume capacities in the range of from about 1 µL to a few nL, e.g. 10-100 nL although other volumes may be utilized readily as well. The fabrication and operation of microfluidics devices as exemplified by the following references are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437.

What is claimed is:

1. An electrical connector, comprising:
   a conformable electrically conductive membrane disposed between a flow cell and an electrical circuitry, the conformable electrically conductive membrane defining conductive pathways between one or more electrical contacts associated with the flow cell and one or more corresponding electrical contacts associated with the electrical circuitry, the conformable electrically conductive membrane comprising an elastomeric material and columns of conductive material, the columns of conductive material defining the conductive pathways, the flow cell having one or more fluid transfer ports, and the flow cell further being associated with at least one electrical component for detecting at least one analyte within the flow cell, the conformable electrically conductive membrane defining a barrier to prevent intrusion of liquid into the electrical circuitry; and
   a clamping member configured to urge the flow cell in proximity to the electrical circuitry with the conformable electrically conductive membrane disposed therebetween establishing the conductive pathways between the flow cell and the electrical circuitry while preventing fluid from contacting the electrical circuitry.

2. The electrical connector of claim 1, wherein the membrane is interposed between the flow cell and the electrical circuitry such that the flow cell and the electrical circuitry are substantially prevented from direct contact with each other.

3. The electrical connector of claim 1, wherein a conformable characteristic of the membrane accommodates surface perturbations present on the flow cell while establishing the conductive pathways between the one or more electrical contacts associated with the flow cell and the one or more corresponding electrical contacts associated with the electrical circuitry.

4. The electrical connector of claim 1, wherein a conformable characteristic of the membrane accommodates at least partial deformation of the flow cell while establishing the conductive pathways between the one or more electrical contacts associated with the flow cell and the one or more corresponding electrical contacts associated with the electrical circuitry.

5. The electrical connector of claim 1, wherein the electrical contacts associated with the flow cell and the corresponding electrical contacts associated with the electrical circuitry comprise a material resistant to galvanic corrosion.

6. The electrical connector of claim 1, wherein the electrical components comprise one or more chemical field effect transistor (chemFET) sensors.

7. The electrical connector of claim 1, wherein the conformable electrically conductive membrane is to isolate the conductive pathways from liquid intrusion.

8. A method for establishing an electrical connection between a flow cell and an electrical circuitry, the method comprising:
   positioning a conformable electrically conductive membrane in proximity to the flow cell and the electrical circuitry, the flow cell having one or more fluid transfer ports, and the flow cell further being associated with at least one electrical component for detecting at least one analyte within the flow cell, the membrane comprising an elastomeric material and columns of conductive material, the columns of conductive material defining conductive pathways;
   urging with a clamping member the flow cell and the electrical circuitry in proximity to one another with the membrane disposed therebetween, whereby the conductive pathways are established between electrical contacts associated with the flow cell and corresponding electrical contacts associated with the electrical circuitry and whereby the membrane forms a barrier to prevent liquid intrusion into the electrical circuitry; and
   transmitting electrical signals from the flow cell through the membrane to the electrical circuitry.

9. The method of claim 8, wherein the membrane is positioned between the flow cell and the electrical circuitry such that the flow cell and the electrical circuitry are substantially prevented from direct contact with each other.

10. The method of claim 8, wherein the flow cell is urged in proximity to the electrical circuitry with the membrane disposed therebetween by a clamping force substantially preventing fluid from contacting the electrical circuitry and establishing the conductive pathways between the flow cell and the electrical circuitry.

11. The method of claim 8, wherein a conformable characteristic of the membrane accommodates surface perturbations present on the flow cell while establishing the conductive pathways between the electrical contacts of the flow cell and the corresponding electrical contacts associated with the electrical circuitry.

12. The method of claim 8, wherein a conformable characteristic of the membrane accommodates at least partial deformation of the flow cell while establishing the conductive pathways between the electrical contacts associated with the flow cell and the corresponding electrical contacts associated with the electrical circuitry.

13. The method of claim 8, wherein the electrical contacts associated with the flow cell and the corresponding electrical contacts associated with the electrical circuitry comprise a material resistant to galvanic corrosion.

14. The method of claim 8, wherein the electrical components of the flow cell comprise one or more chemical field effect transistor (chemFET) sensors configured to detect the at least one analyte in the fluid.

15. An electrical connector for a flow cell, comprising:
   a conductive membrane forming a fluidic barrier between the flow cell and an electrical circuitry to prevent fluid intrusion to the electrical circuitry, the conductive membrane establishing conductive pathways through the conductive membrane, the conductive pathways electrically connecting one or more contacts associated with the flow cell and one or more corresponding contacts associated with the electrical circuitry, the conductive membrane comprising an elastomeric material and columns of conductive material, the columns of conductive material defining the conductive pathways, wherein the one or more corresponding contacts associated with the electrical circuitry and the one or more contacts associated with the flow cell are positioned on opposing sides of the membrane, the flow cell having one or more fluid transfer ports, and the flow cell further being associated with at least one electrical component for detecting at least one analyte within the flow cell, and
   a clamping member configured to urge the flow cell in proximity to the electrical circuitry with the conductive membrane disposed therebetween establishing the conductive pathways between the flow cell and the electrical circuitry while preventing fluid from contacting the electrical circuitry.

16. The electrical connector of claim 15, wherein the flow cell comprises a chemical field effect transistor (chemFET) sensor configured to detect the at least one analyte in fluid contained in the flow cell and configured to generate signals in response to the at least one analyte that are passed to the electrical circuitry through the electrical connector.

17. The electrical connector of claim 15, wherein the conductive membrane is provided with a conformable characteristic that accommodates surface perturbations present on the flow cell while establishing the conductive pathways between the one or more contacts associated with the flow cell and the one or more corresponding contacts associated with the electrical circuitry.

18. The electrical connector of claim 15, wherein the one or more contacts associated with the flow cell and the one or more corresponding contacts associated with the electrical circuitry comprise a material resistant to galvanic corrosion.

19. The electrical connector of claim 15, wherein the conformable electrically conductive membrane is to isolate the conductive pathways from liquid intrusion.

* * * * *